United States Patent
Jin et al.

(10) Patent No.: US 9,315,598 B2
(45) Date of Patent: *Apr. 19, 2016

(54) LOW STRESS FLOWABLE DENTAL COMPOSITIONS

(71) Applicants: Xiaoming Jin, Middletown, DE (US); Paul D. Hammesfahr, Wyoming, DE (US)

(72) Inventors: Xiaoming Jin, Middletown, DE (US); Paul D. Hammesfahr, Wyoming, DE (US)

(73) Assignee: DENTSPLY International Inc., York, PA (US)

( * ) Notice: Subject to any disclaimer, the term of this patent is extended or adjusted under 35 U.S.C. 154(b) by 90 days.

This patent is subject to a terminal disclaimer.

(21) Appl. No.: 13/792,279

(22) Filed: Mar. 11, 2013

(65) Prior Publication Data

US 2013/0190458 A1    Jul. 25, 2013

Related U.S. Application Data

(63) Continuation of application No. 13/473,674, filed on May 17, 2012, now abandoned, which is a continuation of application No. 12/587,199, filed on Oct. 2, 2009, now abandoned, which is a continuation of application No. 11/811,264, filed on Jun. 8, 2007, now abandoned.

(60) Provisional application No. 60/812,541, filed on Jun. 9, 2006.

(51) Int. Cl.
*C08F 2/46* (2006.01)
*C08J 3/28* (2006.01)
*A61K 6/08* (2006.01)
*C08F 22/14* (2006.01)
*A61K 6/083* (2006.01)

(52) U.S. Cl.
CPC .............. *C08F 22/14* (2013.01); *A61K 6/083* (2013.01)

(58) Field of Classification Search
CPC .............. C08F 2/46; C08F 3/24; C08F 3/28; A61K 6/083
USPC .......................................... 522/162, 1; 520/1
See application file for complete search history.

(56) References Cited

U.S. PATENT DOCUMENTS

| | | | |
|---|---|---|---|
| 4,286,047 A | | 8/1981 | Bennett et al. |
| 5,064,746 A | * | 11/1991 | Schwalm ................... 430/270.1 |
| 5,466,721 A | * | 11/1995 | Share .............................. 522/34 |
| 5,506,279 A | * | 4/1996 | Babu et al. ....................... 522/34 |
| 5,609,675 A | | 3/1997 | Noritake et al. |
| 5,760,142 A | | 6/1998 | Klee |
| 5,856,374 A | | 1/1999 | Ono et al. |
| 5,886,064 A | | 3/1999 | Rheinberger et al. |
| 5,998,499 A | | 12/1999 | Klee et al. |
| 6,022,940 A | | 2/2000 | Byerley et al. |
| 6,031,015 A | | 2/2000 | Ritter et al. |
| 6,127,450 A | | 10/2000 | Angeletakis |
| 6,184,339 B1 | | 2/2001 | Stansbury et al. |
| 6,187,836 B1 | | 2/2001 | Oxman et al. |
| 6,204,302 B1 | | 3/2001 | Rawls et al. |
| 6,315,566 B1 | | 11/2001 | Shen et al. |
| 6,709,271 B2 | | 3/2004 | Yin et al. |
| 6,767,955 B2 | | 7/2004 | Jia |
| 6,783,810 B2 | * | 8/2004 | Jin et al. ......................... 427/510 |
| 7,544,721 B2 | | 6/2009 | Gaud et al. |
| 2004/0186195 A1 | | 9/2004 | Suzuki et al. |
| 2005/0182148 A1 | * | 8/2005 | Gaud et al. ......................... 522/1 |
| 2005/0197422 A1 | | 9/2005 | Mayadienne et al. |
| 2008/0076848 A1 | | 3/2008 | Jin et al. |
| 2008/0076853 A1 | | 3/2008 | Jin et al. |
| 2010/0022709 A1 | * | 1/2010 | Jin et al. ......................... 525/50 |

FOREIGN PATENT DOCUMENTS

| | | |
|---|---|---|
| EP | 0282827 A2 | 9/1988 |
| EP | 0373662 A2 | 6/1990 |
| JP | 53099292 | 8/1978 |
| WO | 0168035 A2 | 9/2001 |
| WO | 03082218 A2 | 10/2003 |
| WO | 200585312 A1 | 9/2005 |
| WO | 2006044795 A2 | 4/2006 |
| WO | 2007146239 A2 | 12/2007 |

OTHER PUBLICATIONS

Gunduz, Nazan. Synthesis and Photopolymerization of Novel Dimethacrylates. Master of Science Thesis. (Jun. 8, 1998). pp. 1-170.*

XP-002346645—Application of Diol Dimethacrylates in Dental Composites & Their Influence on Polymerization Shrinkage; Dariusz Bogdal et al; Journal of Applied Polymer Science—vol. 66,2333-337 (1997) John Wiley & Sons.

* cited by examiner

*Primary Examiner* — Sanza McClendon
(74) *Attorney, Agent, or Firm* — Leana Levin; Douglas J. Hura; David A. Zdurne

(57) ABSTRACT

A photopolymerizable and photocleavable (P&P) resin monomer is derived from a reactive photoresponsible moiety via various linkages to form photopolymerizable monomers and/or oligomers.

7 Claims, 1 Drawing Sheet

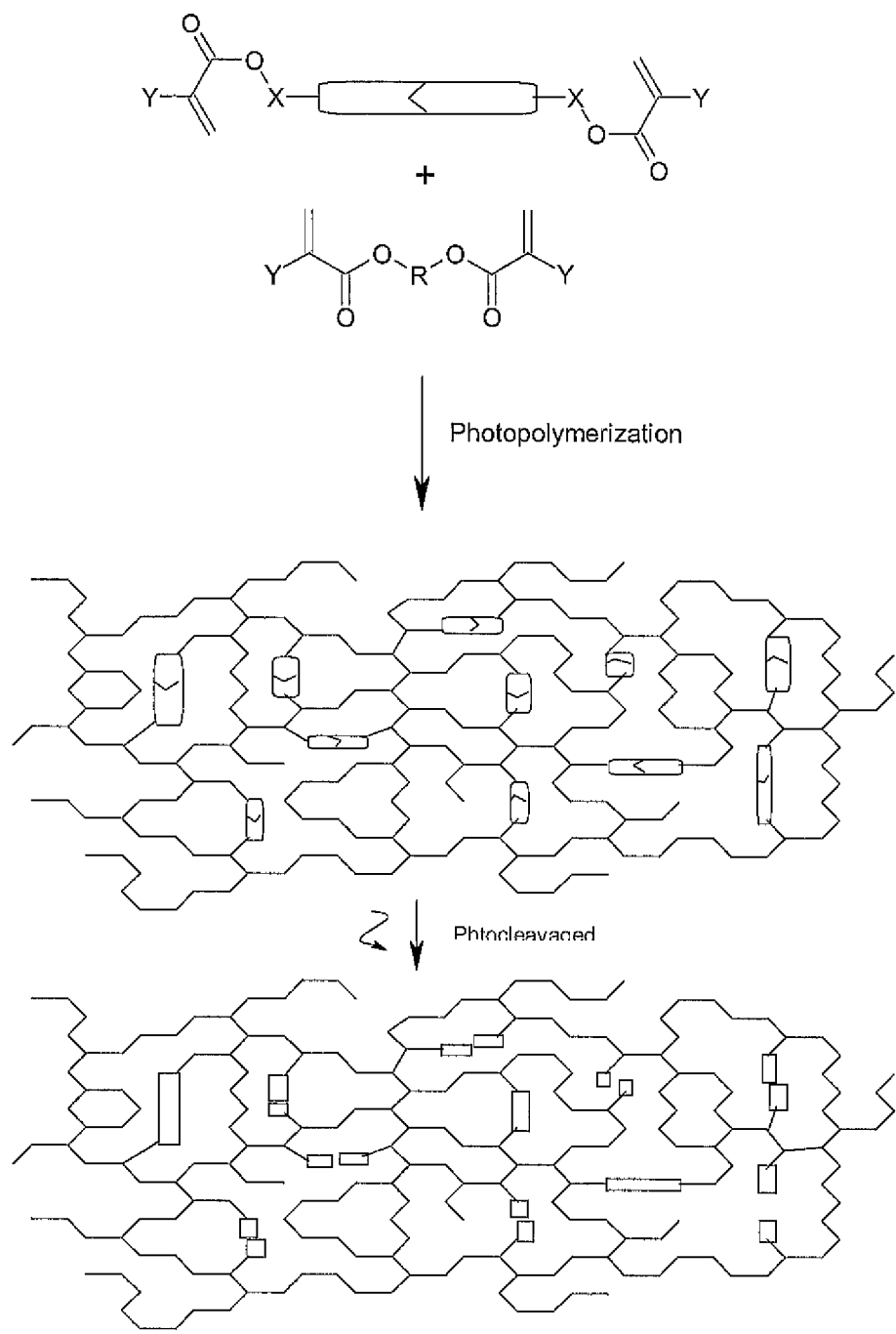
Scheme Illustration for Resin Disclosed Herein and the Cured Networks Therefrom

LOW STRESS FLOWABLE DENTAL COMPOSITIONS

The present application claims priority from U.S. patent application Ser. No. 13/473,674 filed on May 17, 2012, which claims priority to U.S. patent application Ser. No. 12/587,199 filed on Oct. 2, 2009, which claims priority to U.S. patent application Ser. No. 11/811,264 filed on Jun. 8, 2007, which claims priority to U.S. Provisional Application No. 60/812,541 filed on Jun. 9, 2006.

FIELD OF THE INVENTION

This invention relates to photopolymerizable & photocleavable resin monomers and resin composite compositions, which feature by its unique balanced overall performance including very low polymerization shrinkage and very low shrinkage stress as well. The photoreactive moiety incorporated into such new resin's main frame enable to make the resin and/or the cured resin networks that are based upon such resin photocleavable. Thus the polymerization rate of free radical reaction for (meth)acrylate-based resin systems should be substantially reduced since it alter the network formation process and consequently allow the shrinkage stress getting relief significantly. In addition, it is expected that radically polymerizable resin systems containing such P&P resin would find wide range application in microelectronic, special coating and restorative dentistry where the dimensional stability and contraction stress within cured materials are critical to the total performance. The invention also relates to relates to compositions that have exceptionally low curing stress, which are comparable to conventional low stress composite, and have substantial flowability, which is comparable to conventional flowable composite. The dental materials from such compositions with such unique property is for use in the dental arts in the treatment of teeth.

BACKGROUND OF THE INVENTION

Highly cross-linked polymers have been studied widely as matrices for composites, foamed structures, structural adhesives, insulators for electronic packaging, etc. The densely cross-linked structures are the basis of superior mechanical properties such as high modulus, high fracture strength, and solvent resistance. However, these materials are irreversibly damaged by high stresses due to the formation and propagation of cracks. Polymerization stress is originated from polymerization shrinkage in combination with the limited chain mobility. Which eventually leads to contraction stress concentration and gradually such a trapped stress would released and caused microscopically the damage in certain weak zone like interfacial areas. Macroscopically it was reflected as debonding, cracking, et al. Similarly, The origin of contraction stress in current adhesive restorations is also attributed to the restrained shrinkage while a resin composite is curing, which is also highly dependent on the configuration of the restoration. Furthermore, non-homogeneous deformations during functional loading can damage the interface as well as the coherence of the material. Various approaches have been exploring by limiting the overall stress generation either from the restorative materials, or by minimizing a direct stress concentration at the restored interface. It included, for example, new resin, new resin chemistry, new filler, new curing process, new bonding agent, and even new procedure.

There have been tremendous attention paid on new resin matrix development that could offer low polymerization shrinkage and shrinkage stress. For example, various structure and geometry derivatives of (meth)acrylate-based resin systems; non-(meth)acrylates resin systems, non-radical-based resin system. In addition, for light curable, low shrink dental composites, not only new resin systems and new photoinitiators, new filler and filter's surface modification have also been extensively explored, such as filler with various particle size and size distribution, from nanometer to micrometer, different shape, irregular as milled or spherical as-made. It can also be different in composition like inorganic, organic, hybrid. Although an incremental improvement has been achieved with each approach and/or their mutual contribution, polymerization stress is still the biggest challenge in cured network systems.

According to one aspect of the invention, a new kind of resin composition is provided. However, unlike conventional resin system, a new concept is involved in designing such a new resin composition, which would render the polymerization stress in post-gel stage to a subsequent, selective network cleavage in order to have the stress partially released. As mentioned above, all of previous arts towards low shrink and low stress are based on the limitation on the shrink and stress formation in general. However, the shrinkage and stress development in cured network system should have two different stages: a pre-gel phase and a post-gel phase. Actually, most efforts of current arts are focussed on the pre-gel stage and some of them were proved to be effective. Unfortunately, these approaches become ineffective in terms to control the stress development in post-gel stage, where the shrinkage is not as much as in the pre-gel stage but the stress turns to much more sensitive to any polymerization extend. It is the immobility nature of the increasing cross-link density within the curing system that leads to the increasing stress concentration within the curing system, period. Even worse, the problem does not stop here and the trapped stress would eventually get relief from slow relaxation, which can create additional damage on a restored system. Therefore, our approach is based on such a concept that in the post-gel stage if some of "closed net" of any cross-linked system can be selectively broken to promote an extended stress relief period, the total stress concentration would be substantially reduced. To fulfil such a task, a photopolymerizable and photocleavable resin is proposed and a general molecular constitution is designed. It was expected that such a resin monomer can be polymerized like any other resin monomer but its mainframe is able to be triggered to break upon additional light source such as near UV is blended. This is a typical photocleavable process, but it is its capability to be photopolymerized and embedded into a cross-linked system make it unique. In addition, it also makes possible to avoid regenerating any leachable species through such secondary breakage.

Photocleavage is nothing new in solid synthesis of peptides, from which new peptides was directed on certain template in designed sequence, then it was cleaved from its template via a subsequent light exposure. There is no chemical contamination with such a process. On the other hand, photoacid and photobase could be viewed as extended applications for photocleavage. Acidic or basic component is temporally latent to avoid any unwanted interaction with others in the system and they can be released on demand such as light exposure to trigger the regeneration of the acid or base, which then act as normal acidic or basic catalyst for next step reactions. Recently, thermally removable or photo-chemically reversible materials are developed in order to make polymer or polymeric network depolymerizable or degradable for applications such as easily removing of fill-in polymer in MEMS, thermally labile adhesives, thermaspray coatings and removable encapsulation et al. Most recently, photocleavable dentrimers are explored in order to improve the efficiency for drug delivery. Based on our knowledge, there is no prior art involved photocleavable segment in cured network for contract stress control. However, all of those related arts could be used as a practical base to justify this investigation.

Dental composite is formulated by using organic or hybrid resin matrix, inorganic or hybrid fillers, and some other ingredients such as initiator, stabilizer, pigments et al so as to provide with the necessary esthetic, physical and mechanical property for tooth restoration. It is well known that polymerization shrinkage from cured dental composite is one of dental clinicians' main concerns when placing direct, posterior, resin-based composite restorations. Although there are evolving improvements associated with resin-based composite materials, dental adhesives, filling techniques and light curing have improved their predictability, the shrinkage problems remain. In fact, it is the stress associated to polymerization shrinkage that threaten marginal integrity and lead to marginal gap formation and microleakage, which may contribute to marginal staining, post-operative sensitivity, secondary caries, and pulpal pathology.

A common approach to redue the polymerization shrinkage of dental composite is to increase the filler loading, especially for posterior restoration. However, the higher viscosity of these highly filled composites may not adapt as well to cavity preparations. [1-2] It has been demonstrated that to initially place a flowable composites which, with less filler content, have greater flexibility, could reduce microleakage than direct application of microhybrid and packable composite restorations, [3-4] but this benefit may be offset by the increasing polymerization shrinkage for the flowable composite itself. [5] Therefore, it is also highly desirable to develop low shrinkage, especially low curing stress flowable composite, in order to really reduce microleakage as mentioned above.

The challenge in developing any dental composite is to balance the overall performance, including esthetic appearance, handling character as well, in addition to low curing stress and necessary mechanical strength. Unfortunately, superior mechanical strength usually is a result of increasing cross-linking density, from which an unwanted polymerization shrinkage and shrinkage stress always accompanied. There is increasing effort to develop new resin systems in the attempt to minimize such a shrinkage and stress accordingly. For example, reducing the polymerizable proups in the resin matrix by designing resin monomer with different size and shape indeed work well to some extent in this regard. However, it is usually resulted in decreasing mechanical strength and losing certain handling characteristic because of the limited molecular chain mobility and the limited polymerization conversion. In addition the shrinkage can also be reduced by using special filters which allow an increase in filler loading without compromising too much in handling property. Even so, the curing stress from most of flowable composites remains substantially high. Obviously, it is highly desirable to develop flowable dental composition with low curing stress.

DESCRIPTION OF THE PREFERRED EMBODIMENTS

Theoretically speaking, if any kind of environmentally sensitive moiety, such as a thermally cleavable or photo-labile linkage were incorporated into polymerizable resin monomers, such resin or its resulting polymeric material would become command-responsive, more specifically such a resin would be responsive to being thermo-cleavable or photo-cleavable upon exposure to thermal energy or light energy. The chemistry of some classical photo-initiators could be adopted as the base for designing such photopolymerizable and photocleavable resin monomers. However, none of them were really incorporated into polymer chain or polymeric network to make the polymeric chain or network breakable one way or another.

It is the another objective of this investigation to develop a new resin system for next generation low shrink and low stress restorative materials by incorporating a photocleavable or thermally liable moiety as part of a photopolymerizable resin monomer. It was expected that such an unusual approach would enable a polymerized network to be selectively cleaved, thus dispersing the stress from postpolymerization and furthermore to result in a self stress-relief, ultimately to minimize the overall stress concentration.

In order to make a polymerized network cleavable-on-command by light or photocleavable, a light responsive moiety should be stable towards standard light exposure process such as visible light curing until additional exposure to specific light with distinguished energy level. In particular, such energy source can be anything other than the standard visible blue light. Near UV light would be one of typical examples among the many possible choices. Furthermore, it was expected that compounds derivated from ortho-nitrobenzyl segment or from .alpha.-hydroxyalkylphenone should be ideal candidates for this new class resin monomers that be photopolymerized by visible light and be triggered to be breakable by extra UV light if needed.

Scheme I: Typical Polymerizable and Photocleavable Resin Monomer based on α-hydroxyalkylphenone

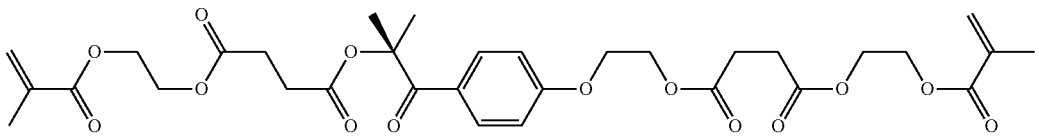

Its feasibility of this approach allows a rapid exploration on its versatility for a new class of resin. Accordingly, a variety of such polymerizable and photocleavable resin monomers were successfully prepared with wide range of viscosity as illustrated in Scheme II.

Scheme II: General Reaction Pathway toward P&P Resin Monomers

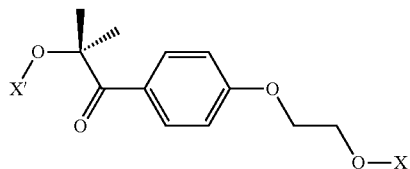

-continued

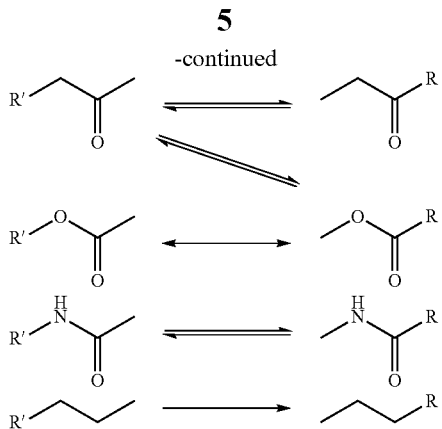

Furthermore, such new resin monomer was formulated with other conventional resin monomers like BisGMA, TEGDMA, UDMA or experimental resin monomer like macrocyclic resin in a variety ratio in order to have overall performance got balanced for the resulting composites. As showed in the following examples, remarkable low shrinkage, low stress and excellent mechanical property plus the good handling characteristics were demonstrated by those composites based on such new class P&P resin monomers.

TABLE I

Polymerization Shrinkage and Stress for Various Activated Resin Mix

| | Shrinkage (%) by Helium Pycnometer | Stress (MPa) by Tensometer |
|---|---|---|
| Denfortex Resin | 10.2 | 4.1 |
| TPH Resin/999446 | 6.8 | 4.5 |
| TPH Resin/999447 | 7.3 | 4.3 |
| Harpoon Resin/xj5-12 | 5.5 | 3.1 |
| Harpoon Resin/xj5-26 | 5.8 | 3.2 |
| LB5-158-1 | 5.2 | 1.4 |
| LB5-158-2 | 5.7 | 2.0 |
| LB5-167-2 | 6.5 | 1.9 |
| LB5-167-3 | 6.2 | 1.5 |
| LB5-167-4 | 6.9 | 1.5 |

TABLE II

Polymerization Shrinkage, Stress and Microstrain for Vaarious Composites

| | Shrinkage (%) by Helium Pycnometer | Microstrain (ue) by Strain Gage | Stress (MPa) by Tensometer |
|---|---|---|---|
| TPH/A2 | 3.10 | 1600 | 2.9 |
| EsthetX/A2 | 2.92 | 1995 | 2.5 |
| SureFil/A | 2.09 | 1840 | 2.7 |
| Supreme/A2B | 2.65 | 1720 | N/A |
| Supreme/YT | 2.39 | 2005 | N/A |
| Harpoon/A2 | 1.34 | 1000 | 1.7 |
| Harpoon/A3.5 | 1.70 | N/A | 1.8 |
| Harpoon/B1 | 1.31 | N/A | 1.5 |
| Harpoon/B2 | 1.61 | N/A | 1.9 |
| Harpoon/CE | 1.70 | N/A | 1.9 |
| LB5-156 | 0.87 | N/A | 1.5 |
| LB5-153 | 0.93 | N/A | 1.4 |
| LB5-160 | 0.36 | N/A | 1.4 |

According to the present invention there is provided a composition of matter that can be polymerized via an energy source, containing portions within the new composition of matter that are reactive to a second energy source. The invention also provides a composition of matter that can be polymerized via an energy source, containing portions within the new composition of matter that are reactive to a second energy source and that upon activation of the second source of energy, de-polymerize and/or degrade. A composition of matter is also provided that can be polymerized via a first energy source, containing portions within the new composition of matter that are reactive to a second energy source and that upon activation of the second source of energy, de-polymerize and/or degrade without substantially effecting the structural properties of the material polymerized by the first energy source. A further composition of matter is provided that can be polymerized via a first energy source, containing portions within the new composition of matter that are reactive to a second energy source and that upon activation of the second source of energy, de-polymerize and/or degrade to elevate stress created during the polymerization of the composition of matter created via the first energy source without substantially effecting the structural properties of the material polymerized by the first energy source. According to another aspect of the invention, a composition of matter is provided that comprises monomers, prepolymers and/or polymers that can be polymerized via an energy source (thermal, photochemical, chemical, ultrasonic, microwave, etc.), containing portions within the new composition of matter that are reactive to a second energy source (thermal, photochemical, chemical, ultrasonic, microwave, etc.).

Thus, certain limitations of the heretofore known art have been overcome. Polymer networks with cross-linking are desired for strength properties, but lead to higher degree of shrinkage and stress. This invention allows formation of cross-linking, while at the same time, providing a mechanism (the second form of energy application) that relieves the stress created while maintaining the structural integrity of the polymer network created. Relief of stress during polymerization has been desired and typically approached through attempt to relieve the stress during the "pre-gel" state of polymerization, prior to the "post-gel" state, wherein the polymer network has now been established, cross-linked set up and, due to the more rigid state, stress is created. The invention substantially eliminates the stress during this "post-gel" state. There are prior known systems for materials that are reversible—that is, once polymerized, some form of post-polymerization energy is applied to fully decompose or degrade the polymer network to a state that renders the material unusable. In the present invention, there is provided only partially, in a controllable manner, degrading or decomposing a portion of the polymer network and maintaining the integrity of the polymer network.

As discussed above, according to one embodiment of the present invention, a photopolymerizable and photocleavable resin monomer (hereinafter referred to as the "P&P" resin) offers unique combination of low curing stress and good mechanical strength. The inventive P&P resin features by incorporating a photoresponsive moiety within the resin monomer and is a (meth)acrylate based resin and capable of being polymerized as any other conventional (meth)acrylate monomers. However, the presence of such a photoresponsive moiety enables P&P resin to polymerize in a way different from those conventional (meth)acrylate monomers. More specifically P&P resin polymerize with a unique curing kinetic, which allow stress relief through the relatively slow curing process without compromising the overall mechanical strength. Consequently substantially low polymerization shrinkage stress results from P&P resin and P&P resin based composite, as compared to those conventional resin like BisGMA/TEGDMA or EBPADMA, and other conventional composites. Typical posterior composites based on the inventive P&P resin and loaded 80-82% (wt/wt) of inorganic fillers offer shrinkage stress of 1.3-1.7 Mpa. They can also demonstrate good mechanical strength. The present invention is extended application of P&P resin. It was unexpectedly discovered that an exceptionally low curing stress remained even with lowering filler loading, which paved a way to low stress flowable composite. The filler level varies from 1% to 70%, wt/wt, preferably, 10-60%, wt/wt, and more preferable 50-60%, wt/wt. The conventional resin monomers can also be incorporated by up to 40-50%, wt/wt with P&P resin, depending upon the nature of such conventional resin monomer and the end use. The filler composition can be adjusted as well.

As shown in Table I through II, an exceptionally low shrinkage stress was revealed from these new flowable compositions. Similar flowable pastes were also formulated by using TPH resin (999446 and available from DENTSPLY International) with the same filler loading and composition as a control. As expected a much higher shrinkage stress resulted, 3.6 MPa vs. 0.9-1.3 MPa. A comparison between the typical experimental flowable composites (LB6-109, 110, 111 and XJ5-196) and some of commercially available flowable materials, such as Dyractflow (DENTSPLY International), AdmiraFlow (VOCO, Germany), Flow It (Jeneric/Pentron, Inc.), EsthetXflow (DENTSPLY International), Revolution (KERR CORPORATION), and Tetric Flow (IVOCLAR VIVADENT, INC.) was performed. There is up to 60-80% (percent) stress reduction achieved by the experimental flowable composite as compared with EstheXflow and Dyractflow. In addition, the new flowable material still offers moderate mechanical strength, which is comparable to most flowable products. It is expected that the mechanical strength can be further improved by refining the filler compositions.

The low stress nature demonstrated by P&P resin and its composites is attributed to the unique curing kinetic as discussed above. PDC study further confirmed this unique, moderately slow polymerization rate as compared to TPH resin or its composite. TetricFlow also demonstrated a slow polymerization rate (under same curing condition) due to the presence of a stable radical compound. TetricFlow has a relatively lower stress than other commercially available flowable materials (3.3-4.6 MPa), but it still generates a much higher shrinkage stress (2.4-3.2 MPa) than the experimental flowable composites based on P&P resin (1.0-1.4 MPa).

The present invention provides flowable composites with an exceptionally low polymerization stress of 0.9-1.3 MPa, which is about 60-70% less than that of typical EsthetXflow (3.4 MPa) or Dyractflow (4.6 MPa). More importantly, the new flowable material can still offer moderate mechanical property. This unique property combination regarding low curing stress and handling character enable to be used as dental restoratives like liners, sealants, et al and other application field where curing stress and flowability is critically concerned.

TABLE I

General Physical Property for Activated Neat P&P Resin Systems

|  | 100% TPH Resin (999452) 0.15% CQ 0.20% EDAB 0.02% BHT | 100% P&P Resin (LB6-71) (w/TEGDMA) 0.15% CQ 0.20% EDAB 0.02% BHT | 100% P&P Resin (EBR6983) (w/TEGDMA) 0.15% CQ 0.20% EDAB 0.02% BHT | 100% TPH Resin (999446) 0.165% CQ 0.30% EDAB 0.025% BHT |
|---|---|---|---|---|
| Lot # | LB5-187-1 | LB6-106-1 | LB6-114 | 030804 |
| Viscosity at 20° C., poise | 150 | 500 | 1020 | 150 |
| Uncured density, g/cm$^3$ | 1.1206 | 1.1129 | 1.1162 | 1.1210 |
| Cured density, g/cm$^3$ | 1.2077 | 1.1888 | 1.1867 | 1.2099 |
| Shrinkage @ 24 hrs., % | 7.2 | 6.4 | 5.9 | 7.4 |
| Stress @ 60 min., MPa | 4.5 | 1.8 | 1.4 | 4.7 |
| $\Delta H_1$ in N2 @ mode 1 |  |  | 110 |  |
| $t_o$, seconds |  |  | 15 |  |
| $t_{max}$, seconds |  |  | 31 |  |
| $\Delta H_1$ in N2 @ mode 2 | 138 | 120 | 107 | 133 |
| $t_o$, seconds | 13 | 17 | 17 | 10 |
| $t_{max}$, seconds | 31 | 35 | 36 | 29 |

TABLE II

Properties of New P&P Resin-Based Flowable Composites

| Pastes | LB6-110 | XJ5-196 | LB6-116 | XJ5-190 |
|---|---|---|---|---|
| Resin Composition | LB6-106-1 (40%) | LB6-106-1 (40%) | LB6-114 (40%) | TPH Resin (40%) |
| Filler Composition | LB6-91-3 (60%) | LB6-91-3 (60%) | LB6-91-3 (60%) | LB6-91-3 (60%) |
| Viscosity at 20° C., poise | 8000 | 4300 | 9300 | 2000 |

TABLE II-continued

Properties of New P&P Resin-Based Flowable Composites

| Pastes | LB6-110 | XJ5-196 | LB6-116 | XJ5-190 |
|---|---|---|---|---|
| PZN Enthalpy ΔH (J/g) by PDC in N2 | (Vis/UV) 46/ | (Vis/UV) 48/ | (Vis/UV) 45/51 | (Vis/UV) 54/ |
| Induction Time $\Delta t_{ini}$ (seconds) by PDC N2 | 17/ | 14/ | 14/13 | 11/ |
| Peak Time $\Delta t_{max}$ (seconds) by PDC in N2 | 34/ | 32/ | 31/29 | 22/ |
| Uncured density (g/cm3) | 1.7201 | 1.7179 | 1.7228 | 1.7294 |
| Cured density (g/cm3) | 1.7875 | 1.7829 | 1.7860 | 1.8049 |
| Shrinkage (%) by pycnometer @ 20 hrs later | 3.8 | 3.6 | 3.5 | 4.2 |
| Shrinkage Stress (MPa) by tensometer | 1.1 | 0.9 | 0.9 | 3.6 |
| Flexural Strength (MPa) | 101 +/− 5 | 109 +/− 6 | 109 +/− 5 | 111 +/− 9 |
| Modulus (MPa) | 4000 +/− 130 | 4700 +/− 190 | 4600 +/− 110 | 5250 +/− 200 |
| Compressive Strength (MPa) | 286 +/− 8 | 277 +/− 13 | 283 +/− 3 | 383 +/− 11 |
| Modulus (MPa) | 5000 +/− 150 | 4900 +/− 450 | 5260 +/− 330 | 4500 +/− 250 |

Thus, it should be evident that the invention as disclosed herein carries out one or more of the objects of the present invention set forth above and otherwise constitutes an advantageous contribution to the art. As will be apparent to persons skilled in the art, modifications can be made to the preferred embodiments disclosed herein without departing from the spirit of the invention, the scope of the invention herein being limited solely by the scope of the attached claims.

What is claimed is:

1. A method of reducing stress during curing of a polymerizable material having a pre-gel phase and a post-gel phase, the method comprising:
    forming a cross-linked network of the polymerizable material by applying a first energy source, and
    selectively cleaving a portion of the cross-linked network by applying a second energy source thereby inducing a stress-relief period, wherein the selective cleaving results in only a partial degradation of the cross-linked network such that the cross-linked network maintains its structural integrity.

2. A method as in claim 1, wherein the polymerizable material is a photopolymerizable and photocleavable resin.

3. A method as in claim 1 wherein the second energy source is ultraviolet light.

4. A method as in claim 2 wherein said resin has a segment selected from the group consisting of ortho-nitrobenzyl and α-hydroxyalkylphenone.

5. A dental material comprising a photopolymerizable and photocleavable resin, wherein said resin forms a cross-linked network upon application of a first energy source and which has a pre-gel and post-gel phase; wherein at least a portion of said cross-linked network is selectively cleavable upon exposure to a second energy source such that the selective cleaving results in only a partial degradation of the cross-linked network such that the cross-linked network maintains its structural integrity.

6. A dental material as in claim 5, wherein said resin has a segment selected from the group consisting of ortho-nitrobenzyl and α-hydroxyalkylphenone.

7. A dental material as in claim 5, wherein the second energy source is in an ultraviolet range.

* * * * *